United States Patent
Mydell

(10) Patent No.: US 10,500,098 B2
(45) Date of Patent: Dec. 10, 2019

(54) EAR COVERING SYSTEM

(71) Applicant: Diana Mydell, Pooler, GA (US)

(72) Inventor: Diana Mydell, Pooler, GA (US)

( * ) Notice: Subject to any disclaimer, the term of this patent is extended or adjusted under 35 U.S.C. 154(b) by 290 days.

(21) Appl. No.: 15/595,230

(22) Filed: May 15, 2017

(65) Prior Publication Data

US 2018/0325198 A1 Nov. 15, 2018

(51) Int. Cl.
*A61F 11/14* (2006.01)
*A61F 11/06* (2006.01)
*H04R 1/02* (2006.01)
*H04R 1/10* (2006.01)
*A45D 44/12* (2006.01)
*A42B 1/06* (2006.01)
*H04R 5/033* (2006.01)

(52) U.S. Cl.
CPC .............. *A61F 11/14* (2013.01); *A61F 11/06* (2013.01); *H04R 1/028* (2013.01); *H04R 1/1016* (2013.01); *A42B 1/06* (2013.01); *A45D 44/12* (2013.01); *H04R 5/033* (2013.01); *H04R 2201/103* (2013.01); *H04R 2201/107* (2013.01); *H04R 2201/109* (2013.01)

(58) Field of Classification Search
CPC ..... A61F 11/14; H04R 1/10; H04R 2201/107; H04R 2201/103; H04R 2201/109; H04R 2201/10; H04R 2201/023; A45D 44/12; A42B 1/06
See application file for complete search history.

(56) References Cited

U.S. PATENT DOCUMENTS

| | | | |
|---|---|---|---|
| 2,325,150 A * | 7/1943 | Sahlmann | A61F 11/06 2/209 |
| 3,112,493 A | 12/1963 | Greenberg | |
| 4,654,898 A * | 4/1987 | Ishikawa | H04R 1/1008 2/209 |
| 4,660,229 A * | 4/1987 | Harris | A61F 11/06 128/866 |
| 4,669,129 A * | 6/1987 | Chance | H04R 1/1008 181/129 |
| 4,791,684 A | 12/1988 | Schwartz | |
| 4,935,965 A | 6/1990 | Wassell | |
| 5,257,420 A * | 11/1993 | Byrne, Jr. | A61F 11/06 2/209 |
| 5,718,001 A * | 2/1998 | Wright | A45D 44/12 128/864 |
| 5,778,455 A * | 7/1998 | Joseph | A45D 44/12 2/174 |
| 5,898,945 A * | 5/1999 | Weiser | A61F 11/06 128/864 |
| D425,671 S | 5/2000 | Cooper et al. | |
| 6,055,672 A | 5/2000 | Natvig | |

(Continued)

*Primary Examiner* — Khaled Annis

(57) ABSTRACT

An ear covering system for keeping ears warm while wearing earphones includes a pair of earphones. Each of the earphones is selectively worn in an associated one of a pair of ears. A pair of earmuffs is provided and each of the earmuffs is selectively worn on an associated one the ears. Each of the earmuffs has a hole therein and each of the earphones is selectively extended through the hole in an associated one of the earmuffs. In this way the earmuffs are worn in conjunction with the earphones. Each of the earmuffs is comprised of a fluid impermeable material to keep the ears warm in a cold environment.

6 Claims, 3 Drawing Sheets

(56) References Cited

U.S. PATENT DOCUMENTS

| | | | |
|---|---|---|---|
| 6,298,493 B1 * | 10/2001 | Ambroise | A45D 44/12 128/866 |
| 6,944,886 B1 * | 9/2005 | Jackson | A45D 44/12 2/209 |
| 7,006,649 B2 * | 2/2006 | Natvig | H04R 1/1058 381/370 |
| D594,601 S * | 6/2009 | Briggs | D29/112 |
| 7,614,089 B2 * | 11/2009 | Hillman-Schwartz | A45D 44/12 128/866 |
| D620,645 S | 7/2010 | Russo et al. | |
| 2005/0132472 A1 | 6/2005 | Allcorn | |
| 2010/0146682 A1 | 6/2010 | Lancaster | |
| 2010/0186146 A1 * | 7/2010 | Askew | A45D 44/12 2/209 |
| 2012/0124719 A1 * | 5/2012 | Michlitsch | A41D 13/05 2/423 |
| 2012/0233742 A1 | 9/2012 | Wood-Bovee et al. | |
| 2013/0195309 A1 | 8/2013 | Tankersley et al. | |

\* cited by examiner

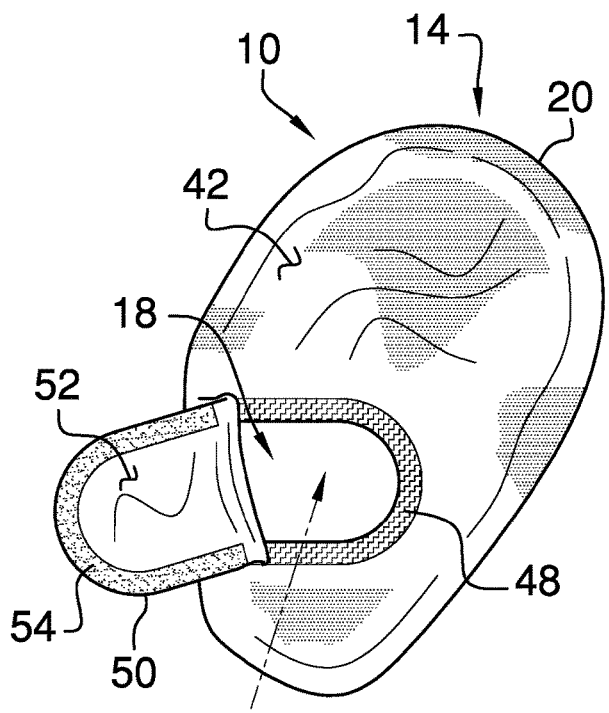
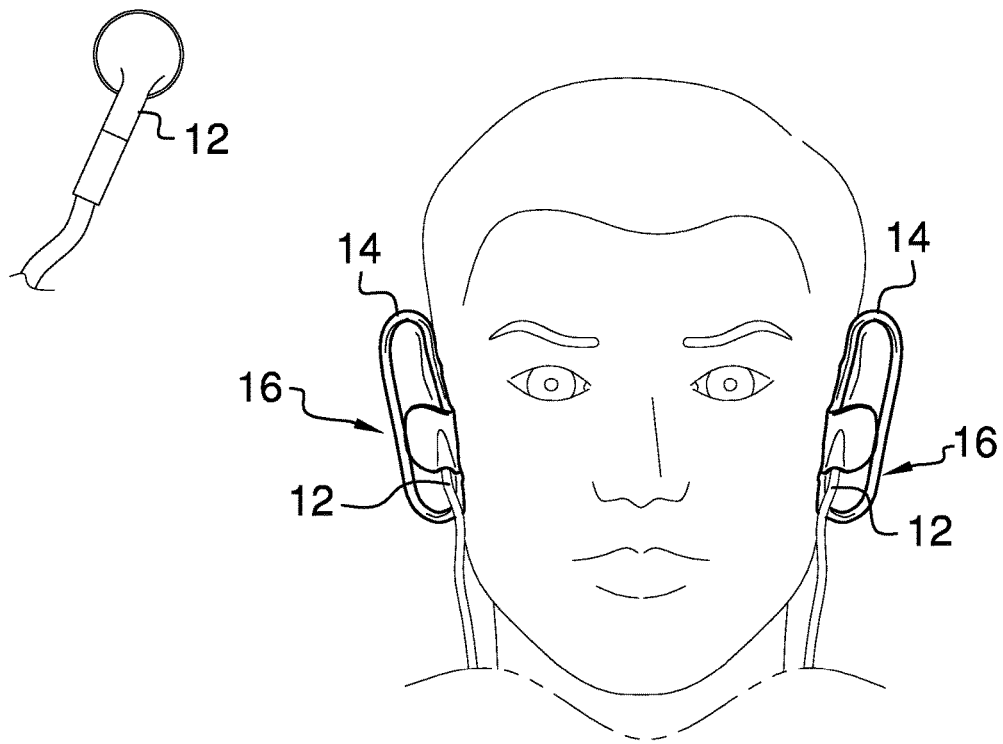
FIG. 3
FIG. 4

EAR COVERING SYSTEM

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION

(1) Field of the Invention

(2) Description of Related Art Including Information Disclosed Under 37 CFR 1.97 and 1.98

The disclosure and prior art relates to covering devices and more particularly pertains to a new covering device for keeping ears warm while wearing earphones.

BRIEF SUMMARY OF THE INVENTION

An embodiment of the disclosure meets the needs presented above by generally comprising a pair of earphones. Each of the earphones is selectively worn in an associated one of a pair of ears. A pair of earmuffs is provided and each of the earmuffs is selectively worn on an associated one the ears. Each of the earmuffs has a hole therein and each of the earphones is selectively extended through the hole in an associated one of the earmuffs. In this way the earmuffs are worn in conjunction with the earphones. Each of the earmuffs is comprised of a fluid impermeable material to keep the ears warm in a cold environment.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein:

FIG. 3 is a front view of an embodiment of the disclosure showing a flap being in an open position.

FIG. 4 is a perspective in-use view of an embodiment of the disclosure.

DETAILED DESCRIPTION OF THE INVENTION

Figure 1:
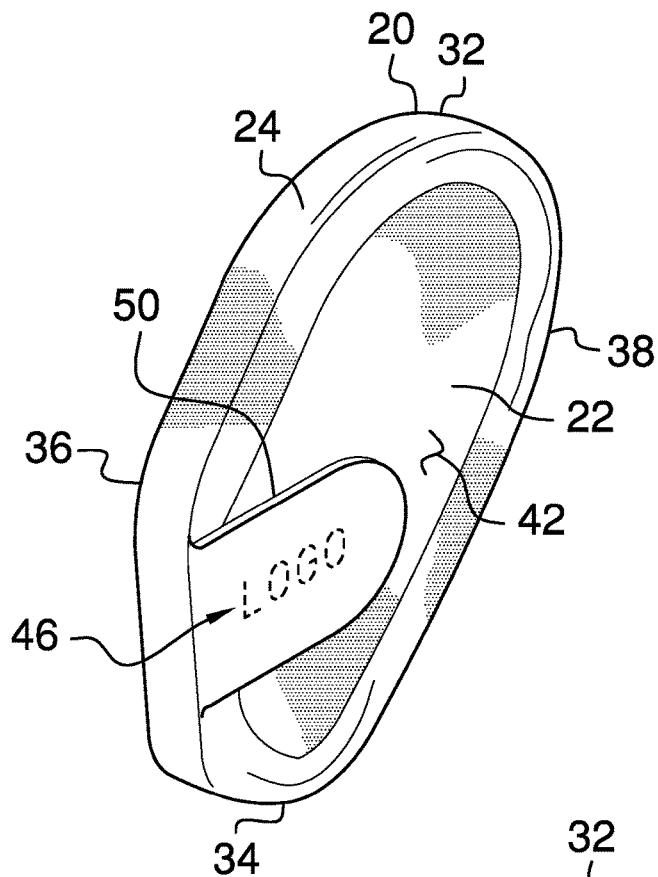
FIG. 1 is a front perspective view of an ear covering system according to an embodiment of the disclosure.
Figure 2:
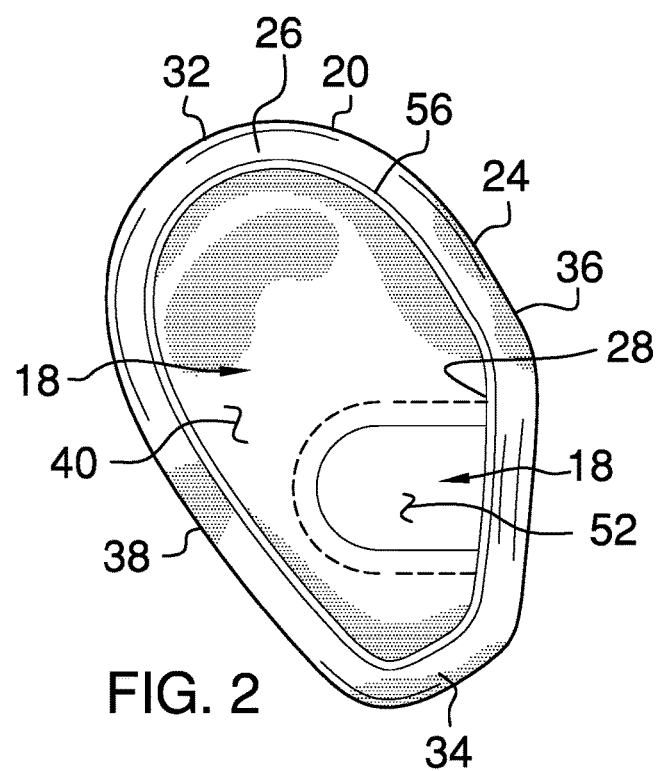
FIG. 2 is a back view of an embodiment of the disclosure.

With reference now to the drawings, and in particular to FIGS. 1 through 5 thereof, a new covering device embodying the principles and concepts of an embodiment of the disclosure and generally designated by the reference numeral 10 will be described.

As best illustrated in FIGS. 1 through 5, the ear covering system 10 generally comprises a pair of earphones 12 and each of the earphones 12 is worn in an associated one of a pair of ears 16. The pair of earphones 12 may comprise electronic earphones 12 such as earbuds or the like. Additionally, the earphones 12 may be electrically coupled to an audio source. A pair of earmuffs 14 is provided and each of the earmuffs 14 is selectively worn on an associated one of a pair of ears 16. Each of the earmuffs 14 has a hole 18 therein and each of the earphones 12 is selectively extended through the hole 18 in an associated one of the earmuffs 14. In this way the earmuffs 14 may be worn in conjunction with the earphones 12. Each of the earmuffs 14 is comprised of a fluid impermeable and thermally insulating material to keep the ears 16 warm in a cold environment.

Each of the earmuffs 14 comprises a cup 20 that has a first wall 22, a perimeter wall 24 and a lip 26 that is coupled to the perimeter wall 24. The lip 26 is spaced from the first wall 22 and the lip 26 has a distal edge 28 with respect to the perimeter wall 24. The distal edge 28 defines an opening 30 into the cup 20 to insertably receive the associated ear 16 having the first wall 22 and the perimeter wall 24 covering the associated ear 16. The cup 20 is comprised of a deformable material to facilitate the cup 20 to be positioned on the ear.

The perimeter wall 24 has a top side 32, a bottom side 34, a first lateral side 36 and a second lateral side 38. The top side 32 curves upwardly between the first 36 and second 38 lateral sides to conform to a top of the ear 16. Each of the first 36 and second 38 lateral sides tapers inwardly between the top side 32 and the bottom side 34 to conform to an earlobe. The first wall 22 has an inside surface 40 and an outside surface 42. Moreover, the hole 18 having a size less than a size of said opening and extends through the outside surface 42 and the inside surface 40. The hole 18 extends from the perimeter wall 24 toward a center of the first wall 22 and the hole 18 has a bounding edge 44.

Indicia 46 may be printed on the outside surface 42 of the first wall 22. The indicia 46 may comprise a logo of a sports team, a logo of a business or any other image. Additionally, the indicia 46 may comprise words corresponding to a selected slogan or any other statement. The cup 20 may be manufactured having a color associated with a professional sports team, a business or any selected color.

A first mating member 48 is coupled to the outside surface 42 of the first wall 22 and the first mating member 48 is coextensive with the bounding edge 44. A flap 50 is coupled to the outside surface 42 of the first wall 22. The flap 50 is positioned in a closed position to cover the hole 18 and the flap 50 is positioned in an open position to expose the hole 18. The flap 50 has an inwardly facing surface 52.

A second mating member 54 is coupled to the inwardly facing surface 52. The second mating member 54 engages the first mating member 48 to retain the flap 50 in the closed position. Each of the first 48 and second 54 mating members may comprise complementary hook and loop fasteners or the like. An elastic member 56 is coupled to the lip 26 and the elastic member 56 is coextensive with the distal edge 28 of the lip 26. The elastic member 56 biases the distal edge 28 to frictionally engage the ear 16 thereby retaining the cup 20 on the associated ear 16.

Figure 5:
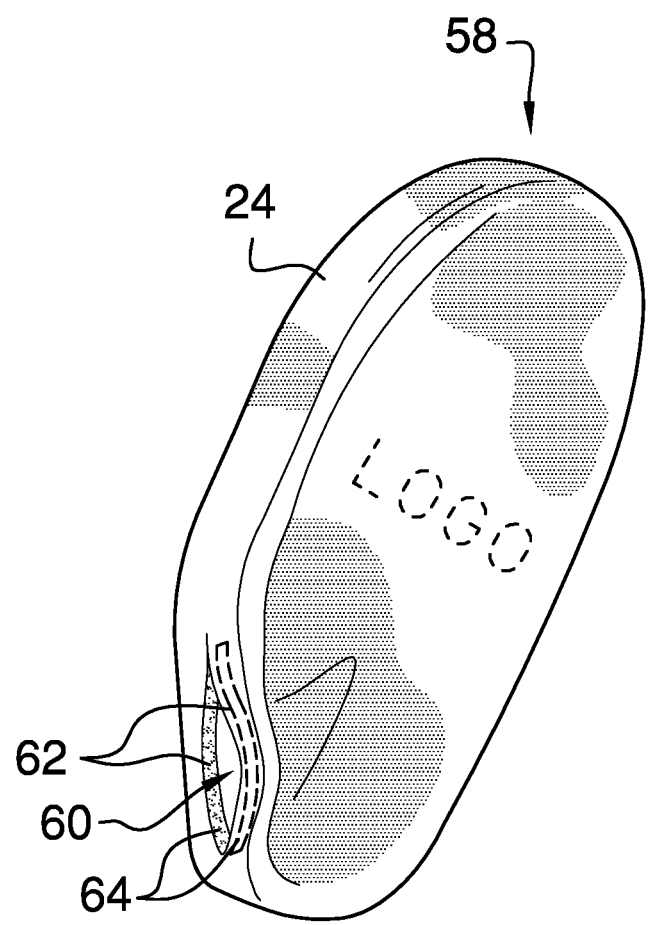
FIG. 5 is a perspective view of an alternative embodiment of the disclosure.

In an alternative embodiment 58 as shown in FIG. 5, the perimeter wall 24 may have a cut 60 extending into the cup 20. The cut 60 has a bounding edge 62 and a pair of mating members 64 may be coupled to the perimeter wall 24. Each of the mating members 64 may be coextensive with the bounding edge 62 of the cut 60 and the mating members 64 may engage each other to close the cut 60. The earphones 12 may be extended through the cut 60 in the associated cup 20 when the earmuffs 14 are worn.

In use, each of the earmuffs 14 is worn on the associated ear 16 in a cold environment to keep the ears 16 warm. The flap 50 on each of the earmuffs 14 is selectively opened to facilitate the earphones 12 to be worn in the associated ear 16. The flap 50 is closed when the earphones 12 are worn and the second mating member 54 is manipulated to engage the first mating member 48. Thus, the flap 50 is closed to facilitate the ears 16 to be kept warm while the earphones 12 are being worn. Each of the earmuffs 14 is worn with or without the earphones 12. A conductor associated with the earphones 12 extends between the flap 50 and the cup 20 when the flap 50 is closed over the earphones 12.

With respect to the above description then, it is to be realized that the optimum dimensional relationships for the parts of an embodiment enabled by the disclosure, to include variations in size, materials, shape, form, function and manner of operation, system and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. An ear covering system comprising:
   a pair of earphones, each of said earphones being configured to be worn in an associated one of a pair of ears; and
   a pair of earmuffs, each of said earmuffs being selectively worn on an associated one of the pair of ears, each of said earmuffs having a hole therein, each of said earphones being selectively extended through said hole in an associated one of said earmuffs thereby facilitating said earmuffs to be worn in conjunction with said earphones, each of said earmuffs being comprised of a fluid impermeable material wherein each of said earmuffs is configured to keep the ears warm in a cold environment, each of said earmuffs comprising
   a cup having a first wall, a perimeter wall and a lip being coupled to said perimeter wall, said lip being spaced from said first wall, said lip having a distal edge with respect to said perimeter wall, said distal edge defining an opening into said cup, said opening being configured to insertably receive the associated ear having said first wall and said perimeter wall covering the associated ear, said first wall having an inside surface and an outside surface, said hole extending through said outside surface and said inside surface opposite to said opening, a size of said hole being less than a size of said opening, said hole extending from said perimeter wall toward a center of said first wall, said hole having a bounding edge, and
   a flap being coupled to said outside surface of said first wall, said flap being positioned in a closed position to cover said hole, said flap being positioned in an open position to expose said hole.

2. The system according to claim 1, wherein said perimeter wall has a top side, a bottom side, a first lateral side and a second lateral side, said top side curving upwardly between said first and second lateral sides wherein said top side is configured to conform to a top of the ear, each of said first and second lateral sides tapering inwardly between said top side and said bottom side wherein said bottom side is configured to conform to an earlobe.

3. The system according to claim 1, further comprising a first mating member being coupled to said outside surface of said first wall, said first mating member being coextensive with said bounding edge.

4. The system according to claim 1, further comprising:
   a first mating member; and
   a second mating member being coupled to said flap, said second mating member engaging said first mating member to retain said flap in said closed position.

5. The system according to claim 1, further comprising an elastic member being coupled to said lip, said elastic member being coextensive with said distal edge of said lip, said elastic member biasing said distal edge to frictionally engage the ear thereby retaining said cup on the associated ear.

6. An ear covering system comprising:
   a pair of earphones, each of said earphones being configured to be worn in an associated one of a pair of ears; and
   a pair of earmuffs, each of said earmuffs being selectively worn on an associated one of a pair of ears, each of said earmuffs having a hole therein, each of said earphones being selectively extended through said hole in an associated one of said earmuffs thereby facilitating said earmuffs to be worn in conjunction with said earphones, each of said earmuffs being comprised of a fluid impermeable material wherein each of said earmuffs is configured to keep the ears warm in a cold environment, each of said earmuffs comprising:

a cup having a first wall, a perimeter wall and a lip being coupled to said perimeter wall, said lip being spaced from said first wall, said lip having a distal edge with respect to said perimeter wall, said distal edge defining an opening into said cup, said opening being configured to insertably receive the associated ear having said first wall and said perimeter wall covering the associated ear, said perimeter wall having a top side, a bottom side, a first lateral side and a second lateral side, said top side curving upwardly between said first and second lateral sides wherein said top side is configured to conform to a top of the ear, each of said first and second lateral sides tapering inwardly between said top side and said bottom side wherein said bottom side is configured to conform to an earlobe, said first wall having an inside surface and an outside surface, said hole extending through said outside surface and said inside surface in a position opposite said opening, said hole having a size smaller than a size of said opening, said hole extending from said perimeter wall toward a center of said first wall, said hole having a bounding edge, a first mating member being coupled to said outside surface of said first wall, said first mating member being coextensive with said bounding edge, a flap being coupled to said outside surface of said first wall, said flap being positioned in a closed position to cover said hole, said flap being positioned in an open position to expose said hole, a second mating member being coupled to said flap, said second mating member engaging said first mating member to retain said flap in said closed position, and an elastic member being coupled to said lip, said elastic member being coextensive with said distal edge of said lip, said elastic member biasing said distal edge to frictionally engage the ear thereby retaining said cup on the associated ear.

* * * * *